US009443631B1

(12) United States Patent
Pan et al.

(10) Patent No.: US 9,443,631 B1
(45) Date of Patent: Sep. 13, 2016

(54) OPTICAL TRAP USING A FOCUSED HOLLOW-BEAM FOR TRAPPING AND HOLDING BOTH ABSORBING AND NON-ABSORBING AIRBORNE PARTICLES

(71) Applicant: U.S. Army Research Laboratory, Adelphi, MD (US)

(72) Inventors: Yongle Pan, Ellicott City, MD (US); Brandon F. Redding, New Haven, CT (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/638,536

(22) Filed: Mar. 4, 2015

(51) Int. Cl.
G21K 1/00 (2006.01)
H05H 3/04 (2006.01)

(52) U.S. Cl.
CPC .............. *G21K 1/006* (2013.01); *H05H 3/04* (2013.01)

(58) Field of Classification Search
CPC .... G01N 21/65; G01N 21/01; G01N 21/658; G01N 15/14; G01N 15/1436; G03H 1/0005; G03H 1/0808; G03H 1/2294
USPC .......... 250/251, 216; 356/300, 301, 36, 445; 359/15; 435/288.7, 34
See application file for complete search history.

(56) References Cited

U.S. PATENT DOCUMENTS 7,515,269 B1 * 4/2009 Alexander ........... G01N 21/658
356/445
8,552,363 B2 * 10/2013 Erickson ........... B01L 3/502761
250/251
8,921,763 B2 * 12/2014 Grier ................... G02B 5/32
250/216
9,222,874 B2 * 12/2015 Hill ..................... G01N 21/01
2013/0341500 A1 * 12/2013 Pascoguin ........... G03H 1/0005
250/251
2014/0004559 A1 * 1/2014 Hill ..................... G01N 21/01
435/34
2015/0377764 A1 * 12/2015 Pan ..................... G01N 15/1436
356/36

OTHER PUBLICATIONS

V. G. Shvedov, A. S. Desyatnikov, A. V Rode, W. Krolikowski, and Y. S. Kivshar, "Optical guiding of absorbing nanoclusters in air.," Opt. Express 17, 5743-5757 (2009).
Y.-L. Pan, S. C. Hill, and M. Coleman, "Photophoretic trapping of absorbing particles in air and measurement of their single-particle Raman spectra.," Opt. Express 20, 5325-5334 (2012).
Ashkin, A. Acceleration and trapping of particles by radiation pressure. Phys. Rev. Lett. 24, 156-159 (1970).
Neuman, K. C. & Block, S. M. Optical trapping. Rev. Sci. Instrum. 75, 2787-2809 (2004).

(Continued)

*Primary Examiner* — David A Vanore
(74) *Attorney, Agent, or Firm* — Eric Brett Compton (57) ABSTRACT

Embodiments of the present invention are directed to systems and methods for trapping and holding airborne particles. In the various embodiments, an optical trap is provided which uses a focused hollow-beam for trapping and holding both absorbing and non-absorbing airborne particles. The optical trap comprises: a trapping region where a particle can be present to be trapped; a light source for generating a coherent beam of light; optics for forming a hollow beam having a ring geometry from the coherent beam of light; and a focusing element for focusing the hollow beam to a point in the trapping region. In this arrangement, the particle is trapped at or near the focal point of the focused hollow beam.

21 Claims, 8 Drawing Sheets

(56) References Cited

OTHER PUBLICATIONS

Desyatnikov, A. S., Shvedov, V. G., Rode, A. V, Krolikowski, W. & Kivshar, Y. S. Photophoretic manipulation of absorbing aerosol particles with vortex beams: theory versus experiment. Opt. Express 17, 8201-8211 (2009).

Pan, Y.-L. et al. Trapping of individual airborne absorbing particles using a counterflow nozzle and photophoretic trap for continuous sampling and analysis. Appl. Phys. Lett. 104, 113507 (2014).

Rohatschek, H. Semi-empirical model of photophoretic forces for the entire range of pressures. J. Aerosol Sci. 26, 717-734 (1995).

Omori, R., Kobayashi, T. & Suzuki, A. Observation of a single-beam gradient-force optical trap for dielectric particles in air. Opt. Lett. 22, 816-818 (1997).

Li, T. Fundamental tests of physics with optically trapped microspheres. (Springer Science, New York, 2013).

Redding, B., Hill, S. C., Alexson, D., Wang, C. & Pan, Y.-L. Photophoretic trapping of airborne particles using ultraviolet illumination. Opt. Express 23, 3630-3639 (2015).

Nieminen, T. A. et al. Optical tweezers computational toolbox. J. Opt. A Pure Appl. Opt. 9, S196-S203 (2007).

Nieminen, T. A. et al. Optical tweezers: Theory and modelling. J. Quant. Spectrosc. Radiat. Transf. 146,59-80 (2014).

\* cited by examiner

A particle below the focus requires a positive $Q_z$ force to push it in the +z direction

FIG. 3(B)

A particle above the focus requires a negative $Q_z$ force to push it in the -z direction

OPTICAL TRAP USING A FOCUSED HOLLOW-BEAM FOR TRAPPING AND HOLDING BOTH ABSORBING AND NON-ABSORBING AIRBORNE PARTICLES

GOVERNMENT INTEREST

The invention described herein may be manufactured, used and licensed by or for the U.S. Government without the payment of royalties thereon.

Research underlying this invention was supported by the Defense Threat Reduction Agency (DTRA) under contract numbers HDTRA1310184 and HDTRA1514122, with U.S. Army Research Laboratory mission funds under Cooperative Agreement Number W911NF-12-2-0019.

BACKGROUND OF THE INVENTION

1. Field

Embodiments of the present invention are generally directed to trapping and holding airborne particles, and more particularly, to optical traps which use a focused hollow-beam for trapping and holding both absorbing and non-absorbing airborne particles.

2. Description of Related Art

Airborne particles pose many problems. The ability to trap airborne particles for inspection and/or measurement is important for many applications. Conventional techniques to optically trap airborne particles use either radiative pressure force or photophoretic force. Trapping a particle in air is more difficult than trapping a particle in a liquid (or on a substrate) since the trap must overcome gravity and air turbulence without help from the higher viscosity of a liquid. Thus, very high numerical aperture (NA) optics, typically in excess of 0.9, is required to produce a strong enough gradient force to trap airborne particles. Trapping airborne particles using the photophoretic force may be advantageous in some cases since the photophoretic force can be 4 to 5 orders of magnitude stronger than the gradient force typically used in optical tweezers.

Existing photophoretic force based traps are only capable of trapping absorbing particles while existing laser tweezer systems can only trap non-absorbing particles. However, many potential applications would benefit from the ability to trap airborne particles regardless of their material type.

BRIEF SUMMARY OF THE INVENTION

Embodiments of the present invention are directed to devices, systems and methods for trapping and holding airborne particles. In the various embodiments, an optical trap is provided which uses a focused hollow-beam for trapping and holding both absorbing and non-absorbing airborne particles.

According to embodiments, the optical trap comprises: a trapping region where a particle can be present to be trapped; a light source for generating a coherent beam of light; optics for forming a hollow beam having a ring geometry from the coherent beam of light; and a focusing element for focusing the hollow beam to a point in the trapping region. In this arrangement, the particle is trapped at or near the focal point of the focused hollow beam.

The optics may comprise a pair of axicons, spatial light modulators (SLM), phase and amplitude mask, biaxial crystals, diffraction pattern, aberration of optical components, and/or an interference pattern of coherent light source using a single or multiple laser beams to produce the hollow beam.

The light source may be a laser, a super-luminescent diode or a super-continuum source. In some instances, the optical trap may further comprise an iris for controlling the diameter of the coherent beam of light.

The trapping region may be located within a containment cell, for instance. Also, the optical trap may comprise other optics, such as a mirror positioned between the optics and the focusing element for changing the direction of the hollow beam. The focusing element may comprise an aspheric lens, an objective or a focusing mirror. It may have a numerical aperture (NA) less than or equal to 0.95, for example. In accordance with the embodiments, the NA of the focusing element should be lower than required for that of a traditional optical trap or laser tweezers.

The optical trap may further include a controller configured to control the trapping and holding of particles. The controller is configured to generate signals to: trap one or more airborne particles in the trapping region; measure one or more properties of the one or more trapped airborne particles; and release the one or more trapped airborne particles.

According to further embodiments, a particle detection and measuring system includes the aforementioned optical trap. In this system, the optical trap is generally configured to trap and hold only about one particle at any one time. Although, the trap could be configured to hold multiple particles if so desired. The particle detection and measuring system may further include one or more of the following: a particle detector configured to detect an airborne particle approaching and/or within the trapping region; at least one source configured to excite emissions of the trapped one or more airborne particles; a measurement device to measure at least one property of the trapped particle; a particle analyzer configured to determine, from the measured property, a parameter related to particle shape, size, refractive index, absorption, or any combination thereof of the trapped one or more airborne particles; and. a particle sorter configured to physically sort, and optionally store, particles based on their measured properties.

The measurement device may be judiciously configured to measure one or more of: imaging, Raman spectra, Raman emission in one or more wavelength bands, laser-induced breakdown emission in one or more wavelength bands, laser-induced breakdown spectra, spark-induced breakdown emission in one or more wavelength bands, spark-induced breakdown spectra, fluorescence in one or more wavelength bands, fluorescence spectra, multi-photon excited fluorescence, thermal emission at one or more wavelengths, thermal emission spectra, or light scattering over one or more angles, light scattering at multiple wavelengths, absorption spectra of the particle, particle size and shape. In some implementations, the particle analyzer is configured to execute an algorithm which identifies or classifies particles into different categories based on their measured properties.

According to additional embodiments, there is a method for continuously sampling particles from air using the aforementioned particle detection and measuring system. The method comprises: continuously directing air including airborne particles toward a trapping region; detecting an airborne particle in the air approaching and/or within the trapping region; trapping one or more airborne particles in the optical trap; measuring a property of the trapped one or more airborne particles; and releasing the trapped one or more airborne particles. The method may further include determining from the measured property a parameter related to particle shape, size, refractive index, absorption, molecular structures and compositions, chemical reactions, or any combination thereof of the trapped one or more airborne particles.

These and other embodiments of the invention are described in more detail, below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments, including less effective but also less expensive embodiments which for some applications may be preferred when funds are limited. These embodiments are intended to be included within the following description and protected by the accompanying claims.

FIGS. 2(A)-(C) show schematics of the cross-sections of the trapping light beam along the direction of propagation involved in forming the optical trap illustrated in FIG. 1.

FIGS. 3(A)-(C) illustrate the focused beam having the ring geometry in more detail and the optical trapping force on a trapped airborne particle according to the present invention.

FIGS. 4(A) and (B) are photographs of the trapping region in the optical trap according to an embodiment of the present invention.

FIGS. 5(A)-(D) show plots of numerical simulated data for different optical traps.

FIGS. 6(A) and (B) are plots showing the force along the optical axis experienced by a particle with radius of $5\lambda$ and n=1.5 for a traditional laser tweezers and an optical trap of the present invention having a hollow beam with a ring geometry. FIG. 6(A) shows the force using a full lens, as in a traditional laser tweezers, while

DETAILED DESCRIPTION

A novel optical trapping apparatus and methods for using the same are disclosed. This innovative optical trapping technique utilizes the radiative pressure of light to trap and hold transparent (non-absorbing) airborne particles while the photophoretic force is able to trap absorbing particles in the same optical geometry formed of a single shaped laser beam. The radiative pressure force results from the transport of momentum from photons to a particle. More particularly, radiative pressure forces are a combination of a gradient force and a scattering force. If a particle is near the focus of a laser beam, the gradient force will pull the particle back toward the high intensity region at the focus, providing the restoring force required to trap a particle. On the other hand, the scattering force, which results from the transfer of momentum from photons scattered off a particle, pushes the particle in the direction of light propagation and does not provide the required restoring force. Roughly speaking, optical trapping is possible when the gradient force overcomes the scattering force.

By comparison, the photophoretic force results from the interaction between a heated particle and the surrounding gas molecules. If a light beam impinges on an absorbing particle, some of the light will be absorbed and converted to heat. In particular, if a particle is heated asymmetrically (e.g. if a strongly absorbing particle is illuminated from one side), then gas molecules on the higher temperature side of the particle will also heat up and subsequently collide with the particle at higher velocities, imposing a net force pushing the particle toward its cold side. For a strongly absorbing particle, this photophoretic force can be 4 to 5 orders of magnitude stronger than the gradient force typically used in optical tweezers.

The innovative optical trap is formed by a single shaped focusing laser beam. In optical traps according to the present invention, the focused beam is a hollow beam having a ring or ring-like geometry or profile, i.e., the center of the beam is removed where the contribution to the incident photon momentum along the optical axis is strongest. This effectively reduces the scattering force along the optical axis such that the gradient force is sufficient to achieve optical trapping at a much lower numerical aperture (NA) of focusing optics than used by a conventional optical trap such as laser tweezers. The use of a single focus beam enables simple alignment and the use of low NA focusing optics will make the trapping system easily integrate with additional optical characterization tools. This greatly increases the versatility of the optical trap.

Numerical simulations are presented herein to guide the design of the hollow-cone in order to enable trapping of various types of particles. This technology has been demonstrated for trapping of both absorbing and transparent particles with either spherical or spatially irregular geometries. Such a general purpose optical trapping scheme could enable on-line characterization of arbitrary airborne particles.

Figure 1:
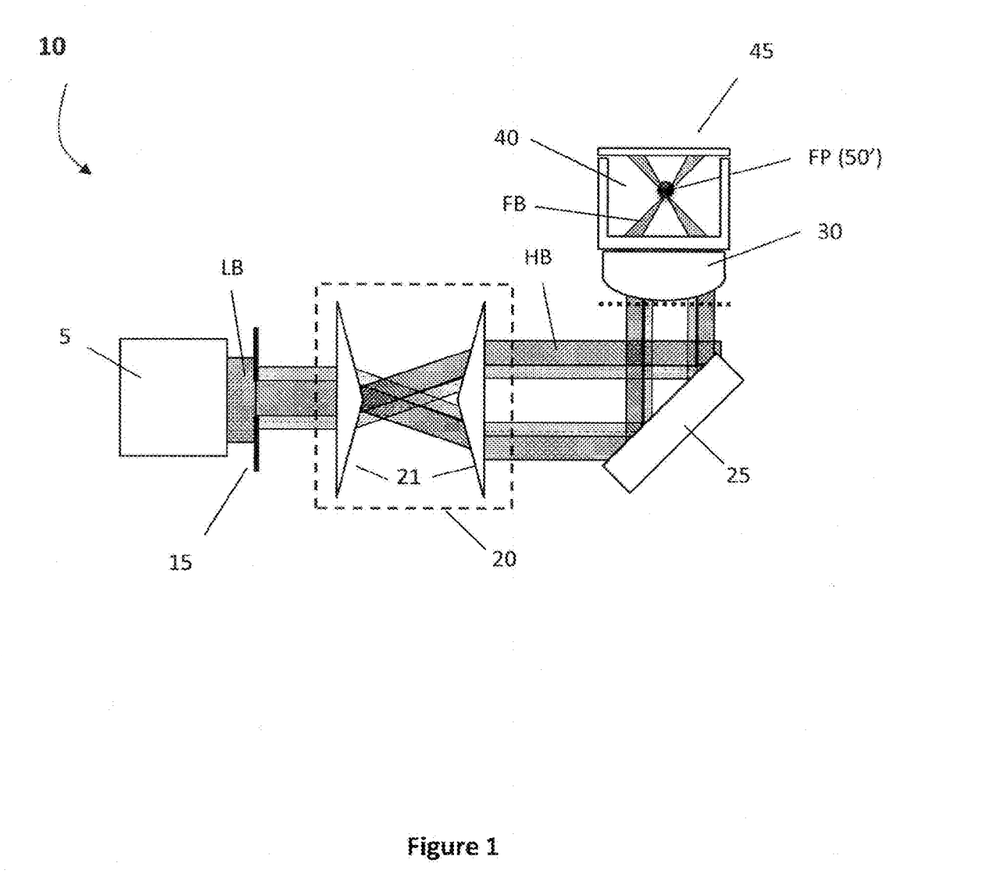
FIG. 1 shows a schematic illustration of an optical trap according to an embodiment of the present invention.

FIG. 1 shows a schematic illustration of an optical trap 10 for trapping particles according to an embodiment of the present invention. The optical trap 10 is specifically configured to generate a hollow beam of light having a ring geometry which when focused can trap and hold an airborne particle.

Laser 5 generates a laser beam and is expanded into a collimated beam with diameter D (see FIG. 2 (A)) indicated here as laser beam LB. The particular wavelength of light used is not believed to be critical for the trap 10, although there may be a multitude of reasons for selecting a particular laser. The laser light may be in the ultraviolet (UV), visible, and/or infrared (IR) wavelength region, for example. In one exemplary embodiment, laser 5 may be an Ar-ion laser diode operating at a wavelength $\lambda$ of 488 nm in continuous wave (CW) mode and providing approximately 750 mW of power. In lieu of an actual laser, a light source with a high spatial coherence could be used to form the equivalent to laser beam LB having a focal spot with high power, such as a super-luminescent diode or a super-continuum source.

An iris 15 may be used to adjust or tune the diameter of the laser beam LB. The iris 15 may be comprised of multiple blades (e.g., 9 or 15), driven by a motor (not shown), which form an adjustable sized diaphragm opening. The iris is not strictly required for all embodiments. The laser beam could be expanded to the appropriate diameter with the laser 5 and/or other optics, instead of over-expanding and then using the iris 15 as is shown in FIG. 1. A depiction of the cross-section of the laser beam LB along the direction of propagation is shown in FIG. 2(A). In one exemplary embodiment, the laser beam before the iris had a diameter of approximately 2 cm and after the iris it was reduced the size to about 1 cm or less. This may depend on the optics used.

Optics 20 take the laser beam LB and form a hollow beam HB profile. Optics 20 may include a set of one or more typical optical elements used for shaping light. The hollow beam HB is shaped like a ring, that is, an annular region with a central opening or void. Such a ring geometry or profile can be generated by holography, spatial light modulators (SLM), phase and amplitude mask, biaxial crystals, diffraction pattern, aberration of optical components, or interference pattern of coherent light source using a single or multiple laser beams as known in the art. Here, optics 20 are shown as configured as a pair of axicon lenses 21.

The inner diameter of the hollow beam HB is controlled with the tunable iris 15 before passing through the optics 20 to form a collimated hollow beam at the back focal plane of the lens 30. The inner diameter of the hollow beam is adjusted to form an inner NA of the conically focusing region to form a strong enough stable trapping conditions. As the iris is closed, the ring width becomes narrower. Conversely, when the iris is open, the ring width becomes wider. A depiction of the cross-section hollow beam HB along the direction of propagation is shown in FIG. 2(B). The light beams are indicated in grey. The lighter grey rays depicted the variable inner diameter of the hollow beam HB.

The outer diameter of the hollow beam HB may be controlled by relative focal length of the optics 20 (e.g., the pair of axicons 21), which act as a beam expander in addition to forming the ring shape of the hollow beam HB. The outer beam diameter should be expanded to match the diameter of the focusing lens 30 to gain the highest outer NA The focusing lens 30 may be include the aspheric lens 30 (as shown), or alternatively or additionally, an microscopic objective or a reflective focusing mirror (parabolic or spherical reflector). In general, the hollow beam HB is expanded to match the diameter of focusing optics (lens, objective, or mirror) before being focused. For a lens with outer diameter of 24 mm, and focal length of 18 (NA outer=0.55), the inner diameter could be about 21 mm, corresponding to NA inner=0.5, for example.

Once the inner and outer diameters of the hollow beam HB have been set, the trap can be used for most particles without changing these parameters. The hollow beam would generally stay the same and be turned 'on' to hold a particle in place and then the laser beam could be turned 'off' or blocked altogether (e.g., with a shutter) to release a particle.

After passing the optics 20, the hollow beam HB is directed to the back focal plane of the optical focusing element, such as lens 30, as shown. The hollow beam HB then passes through the lens 30 which focuses it into a trapping region 40. A depiction of the cross-section of the focused hollow beam FB along the direction of propagation is shown in FIG. 2(C). In some embodiments, the trapping region 40 may be a glass containment cell. This arrangement helps to minimize air turbulence near the trapping position. The focal point FP is formed within the trapping region 40.

In some embodiments, additional optics can be interposed along the beam path. As shown in FIG. 1, a mirror 25 is provided which changes the directed to the hollow beam HB. This enables a more compact system and/or the direction of the hollow beam HB to be changed. It is believed that the trap will work most efficiently if the light is propagating upward (against gravity) in the focal region. It should also work with the light travelling with gravity (i.e. aimed down). If the cone is formed sideways the photophoretic trapping may not be as efficient.

The lens 30 forms a hollow conical focus within the trapping region where airborne particles are present. The lens 30 may be an aspheric lens, for instance. It may be formed of glass, polycarbonate, or other materials having a refractive index of about 1.3-3.9 as an example. The lens 30 may has a numerical aperture (NA) preferably less than or equal to 0.95. For instance, it could be 0.55-0.95. In one particular embodiment, it is approximately 0.55. However, the optical focusing element could alternatively be a microscopic objective or a reflective focusing mirror (parabolic or spherical reflector) instead of lens 30 in other embodiments.

Particles 50 in the trapping region 40 can be trapped and held by the focused beam FB having the hollow or ring geometry. A trapped particle is indicated at 50'. The size of the particles 50 may vary depending on the environment and/or desired application(s). Airborne particles ranging from 0.6 to 100 micrometers may be quite common in some environments. Typical sizes of a single or aggregates of a group of bacteria and bacterial spores may range from 0.6 to 10 μm. Typical sizes of anthrax spores range from 1.1 to 1.7 μm in length and 0.8 to 0.9 μm in diameter. Typical sizes of fungal spores may range 2 to 20 μm in diameter. Pollens typically can be 5 to 100 μm in diameter. These exemplary particles as well as other larger or smaller in diameters should be able to be held with the trap 10. Typically, it is envisioned that the optical trap 10 will trap and hold only about one particle at any one time. Although, simultaneous trapping of multiple particles can be realized by forming multiple conically focusing regions using holography, SLM, or interference pattern, for instance.

While a particle 50' is trapped and held in the optical trap 10, one or more properties of that trapped particle 50' may be measured or otherwise made. One or more measuring devices may be positioned proximate to the trapping region 40 for this purpose. There may be a window or opening 45 in the trapping region 40 to enable measurement of trapping particles to be made. The window may be made of glass or other light transparent material. In FIG. 1, the window 45 is shown as being opposed to the lens 30. However, this is merely illustrative and it will be appreciated that it may be placed at other locations relative to the trapping region 40. Also, there may be multiple windows 45 for multiple measurements apparatus at any desired locations, such as surrounding the trapping region 40 also.

The measuring device may be a camera or other measurement device that is configured to inspect or measure at least one property of the trapped particle 50' while it is held in the optical trap 10. These measurements may include, for example, Raman, fluorescence, thermal emission, laser-induced breakdown spectroscopy (LIBS), spark-induced breakdown spectroscopy (SIBS), elastic scattering over one, a few or many angles or wavelengths. The Raman, fluorescence, thermal emission, LIBS and SIBS may each be measured at one or more emission bands, including the case of sufficient bands to be considered a spectrum. The foregoing list is not exhaustive and other measurement techniques may be used. Devices for performing such measurements are generally known and will not be described in greater detail.

Figure 2A:
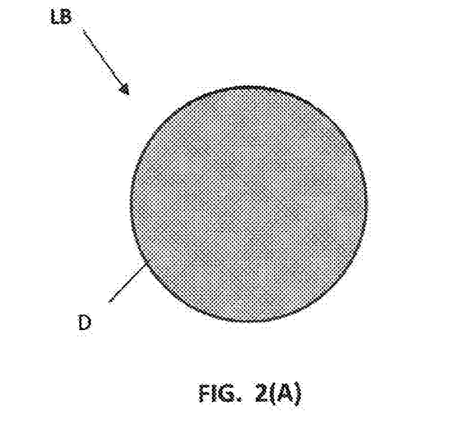
FIG. 2(A) is a schematic of the transverse cross-section of the initial laser beam from the laser.
Figure 2B:
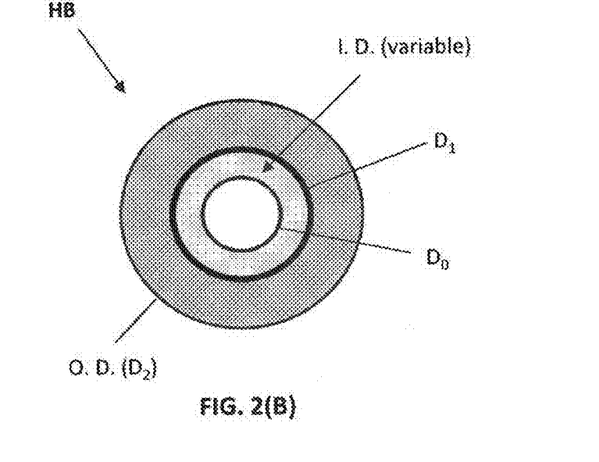
FIG. 2(B) is a schematic of the transverse cross-section of the hollow beam having a ring geometry formed by the optical system.
Figure 2C:
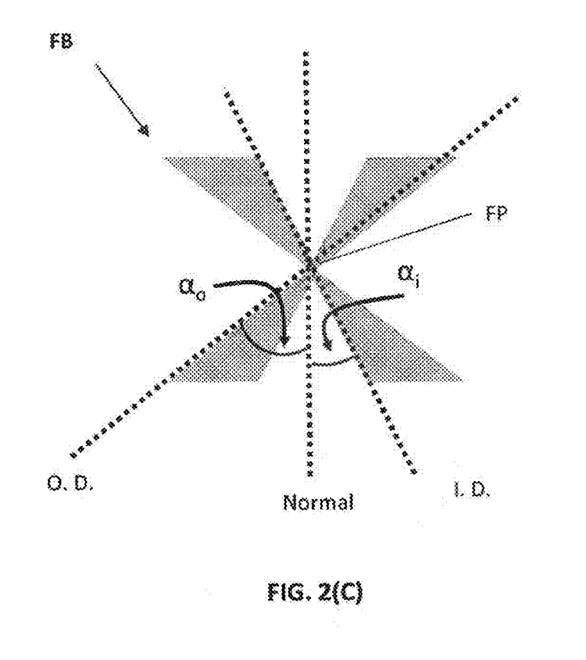
FIG. 2(C) is a schematic of the longitudinal cross-section of the hollow beam along the optical axis after being focused by the focusing element into the trapping region.

FIGS. 2(A)-(C) show schematics of the cross-sections of the light beams along the direction of propagation involved in forming the optical trap 10 illustrated in FIG. 1. In actuality, these beams are one contiguous beam of light which is manipulated at different points as it propagates. To begin, FIG. 2(A) is a schematic of the transverse cross-section of the expanded laser beam LB. It is generally circular and has a diameter D defined by the laser 5. Its diameter can be further adjusted by the iris 15 to a desired diameter or directly expanded to a desired diameter. FIG. 2(B) is a schematic of transverse the cross-section of the hollow beam HB. Optics 20 takes the laser beam LB and forms a hollow beam HB. The hollow beam HB is shaped like a ring, that is, as an annular region with a central void. It is defined by an inner diameter I.D. and an outer diameter O.D. The inner diameter I.D. is variable or adjustable and controlled by the iris 15. It may vary between a minimum inner diameter $D_0$ and a maximum inner diameter $D_1$. The outer diameter is $D_2$. As the iris 15 is closed, the ring width (i.e., the distance between the inner and outer diameter) becomes narrower. And conversely, as the iris 15 is opened, the ring width becomes wider. FIG. 2(C) is a schematic of the longitudinal cross-section of the focused beam FB. The optical trapping geometry can then be described by the outer NA, which is fixed by the lens 30 or other focusing element, and the inner NA which can be continuously adjusted using the iris 15. The conical focus of the beam FB is defined by the NA of the lens, $NA_o = n \sin(\alpha_o)$, and the inner NA of the hollow region, $NA_i = n \sin(\alpha_i)$, as shown. By adjusting the beam size before the optics 20 (e.g., the axicon lenses 21) with the tunable iris 15, the size of the inner hollow region, i.e. $NA_i$, can be continuously adjusted (as indicated by the light grey region). The angle $\alpha_o$ is defined as the angle to the outer diameter of the focused beam FB. The angle $\alpha_i$ is defined as the angle to the inner diameter of the focused beam FB. The angles $\alpha_o$ and $\alpha_i$ are measured from the line normal to the lens 30.

Figure 3A:
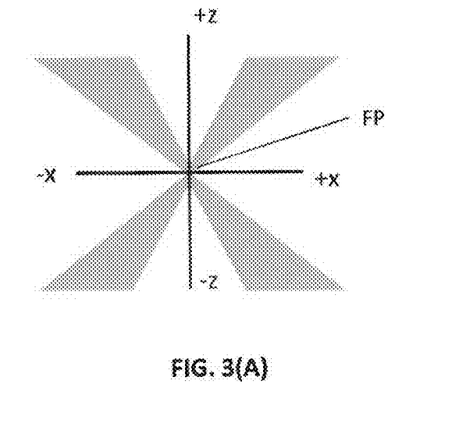
FIG. 3(A) shows the longitudinal cross-section of the focused beam when no particle is presently trapped there.
Figure 3B:
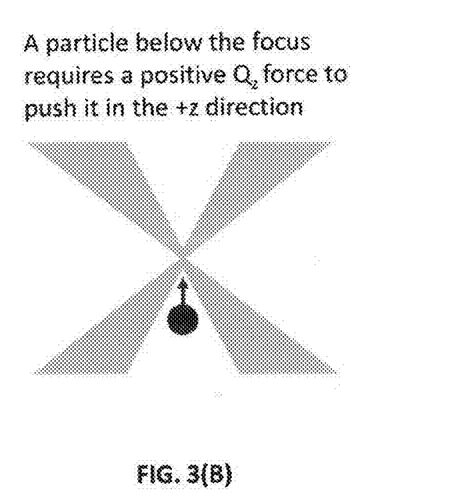
FIG. 3(B) shows the force required to act on a particle which drifts below the focal point of the focused beam to achieve a stable trap.
Figure 3C:
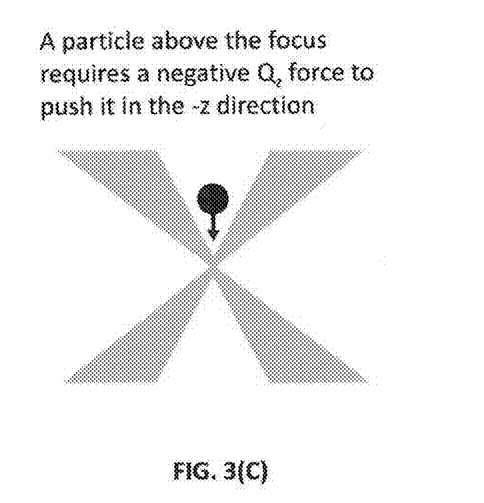
FIG. 3(C) shows the force required to act on a particle which drifts above the focal point of the focused beam to achieve a stable trap.

FIGS. 3(A)-(C) illustrate the longitudinal cross-section focused beam FB in more detail and the optical trapping force on a trapped airborne particle. FIG. 3(A) shows the focused beam FB. The beam is conical with a longitudinal cross-section depicted in the x-z plane. No particle is presently trapped here, but would be held at or near the focal point FP (x, y, z=0, 0, 0). The beam has a hollow ring shape. The focusing optics (e.g., lens 30) focuses the light such that it is collimated and contracts towards the focal point and expands and diverges thereafter. The focal point FP is not an infinitesimal point, but in actuality is a small area limited by the wavelength of light, i.e. the diffraction limit, approximately $\lambda/2$. FIG. 3(B) shows when a particle drifts below the focal point. A particle below the focus requires a positive $Q_z$ force to push it in the +z direction. FIG. 3(C) shows when a particle drifts above the focal point. A particle above the focus requires a negative $Q_z$ force to push it in the −z direction. The focused beam FB generates a restorative force which urges the particle back toward the focal point FP. While the above-description refers to particle displacement in the z direction, it will be appreciated that the particle displacements in the x- and/or y-directions will be similar.

Figure 4A:
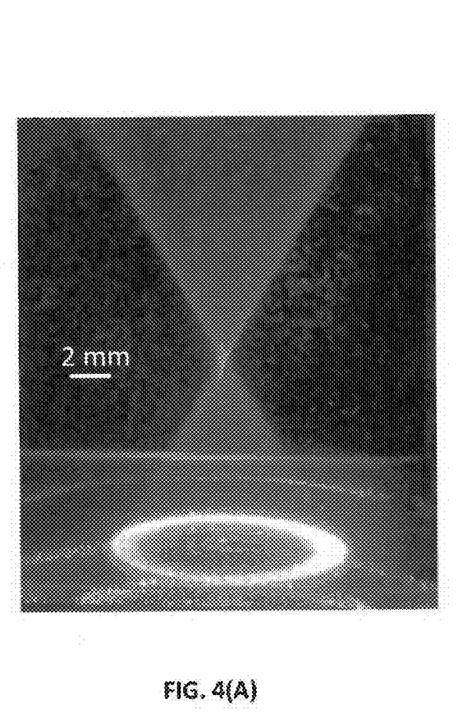
FIG. 4(A) is an image of an actual focused beam having a ring geometry formed by the optical trap.
Figure 4B:
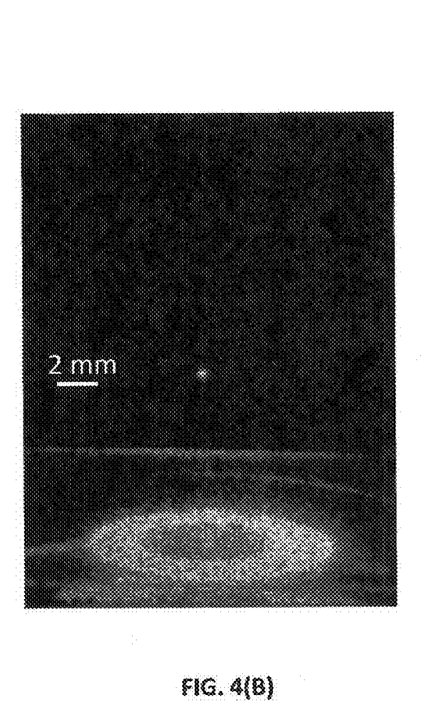
FIG. 4(B) shows a single grass spore trapped near the focal point of the focused beam.

FIGS. 4(A) and (B) are photographs of trapping region 40. FIG. 4(A) is an image of an actual conical focal region produced inside a glass containment cell. This image was obtained by using a long exposure time while introducing a large quantity of Johnson Smut Grass spores into the glass containment cell. After the particles settle, a single spore remains trapped near the focal point spot, as shown in FIG. 4(B). The smut grass spores are strongly absorbing and thus the photophoretic force is dominant and the particle is trapped in the low-intensity region just above or below the focal point.

FIGS. 5(A)-(D) show plots of numerical simulated data for an optical trap according to embodiments of the present invention. The optical trap 10 shown in FIG. 1 can also be used to trap transparent particles. In order to optimize the trapping geometry for transparent particles, full-wave simulations were performed for analyzing the trapping force acting on a particle for the hollow cone geometry. These simulations were performed using the software application called "Optical Tweezers Toolbox." This software application is implemented in Matlab, for the computational modeling of optical tweezers. The toolbox is designed for the calculation of optical forces and torques, and can be used for both spherical and non-spherical particles, in both Gaussian and other beams. The toolbox might also be useful for light scattering using either Lorenz-Mie theory or the T-matrix method. It is available online at: http://www.physics.uq.edu.au/people/nieminen/software.html. The simulations assumed spherical particles in air with a diameter of $10\lambda$ (i.e., approximately 4 μm based on the exemplary illumination wavelength $\lambda$ of 488 nm).

Figure 5A:
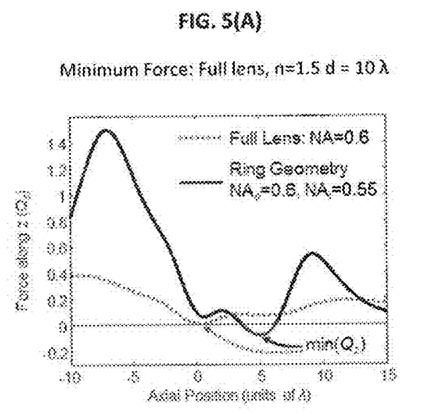
FIG. 5(A) is a plot showing the optical trapping force along the optical axis experienced by a particle with a diameter of $10\lambda$ and refractive index of 1.5 using a lens of NA=0.6 for a traditional laser tweezers (dashed line) and an optical trap of the present invention having a hollow beam with a ring geometry (solid line).

In FIG. 5(A), there is a plot showing the optical trapping force along the optical axis experienced by a particle with a diameter of $10\lambda$ and refractive index of 1.5 and using a lens of NA=0.6 for different optical trapping means. Data for a "full lens" (using ordinary focused lens as in a conventional optical tweezers) and "ring geometry" (using the conical ring-shaped focused hollow beam as in the optical trap of the present invention) are detailed. The trapping force is expressed in terms of the dimensionless quantity $Q_z$ which is related to the actual force acting on the particle as $F_z = Q_z P n/c$, where P is the incident laser power, n is the refractive index of the particle and c is the speed of light. (For a discussion of the forces acting on absorbing particles, additional reference is made to Yong-Le Pan, et al. "Trapping of individual airborne absorbing particles using a counterflow nozzle and photophoretic trap for continuous sampling and analysis," Applied Physics Letters 104, 113507 (2014), herein incorporated by reference.).

The dotted line shows the force experienced using the full lens as in a conventional single-beam optical trap as laser tweezers (i.e. without the pair of axicons 21 shown in FIG. 1), and the solid line shows the force experienced using the ring illumination geometry of the optical trap shown in FIG. 1. In both cases, the outer NA is set to 0.6 and for the ring geometry the inner NA is set to 0.55. The trapping force is presented as a function of position along the optical axis z, where the focus is formed at z=0. In order to achieve optical trapping, a negative restoring force is required. As shown in FIG. 5(A), a negative force is achieved using the ring geometry, but not using the full lens when the outer NA is set to 0.6. This can be understood as a trade-off between the scattering force and the gradient force. In a single beam geometry using the full lens, a much higher NA is required to obtain a gradient force which is stronger than the scattering force. For this reason, single-beam optical trapping geometries typically have to use a very high NA. In the ring geometry, the center of the beam is removed from where the contribution to the incident photon momentum along the optical axis is strongest. This effectively reduces the scattering force along the optical axis such that the gradient force is sufficient to achieve optical trapping at a much lower outer NA.

Figure 5B:
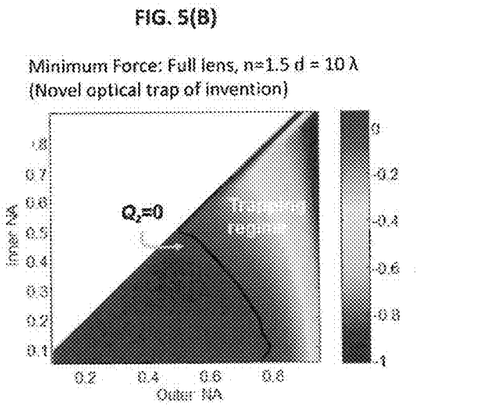
FIG. 5(B) is a plot showing the minimum trapping force experienced by a particle with radius of $5\lambda$ and refractive index of 1.5 using the novel ring geometry with varying inner and outer NA of the hollow beam.

FIG. 5(B) is a plot showing the minimum trapping force experienced by a particle with radius of 5λ and refractive index of 1.5 using the ring geometry with varying inner and outer NA of the hollow beam, as shown in FIG. 2(A). Optical trapping is possible when a negative $Q_z$ force is obtained. The black contour line indicates a force of $Q_z=0$ and combinations of outer and inner NA which allow for optical trapping are indicated as the "trapping regime." It was found that for a relatively narrow ring (i.e. where the inner NA is only slightly less than the outer NA), optical trapping is possible for an outer NA as low as 0.55. To illustrate the advantage of using a ring geometry as opposed to the "full lens" approach taken in standard laser tweezers, we simulated the minimum trapping force as a function of the outer NA and the refractive index of the particle as shown in FIGS. 5 (C) and (D).

Figure 5C:
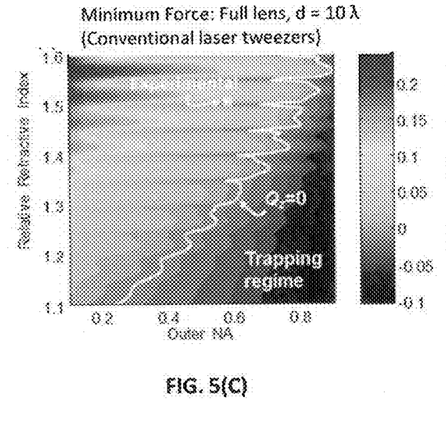
FIG. 5(C) shows the minimum trapping force obtained using the full lens of a traditional laser tweezers and FIG. 5(D) shows the minimum trapping force obtained using the novel ring geometry of the optical trap of the present invention as a function of the outer NA and the refractive index of the particle.
Figure 5D:
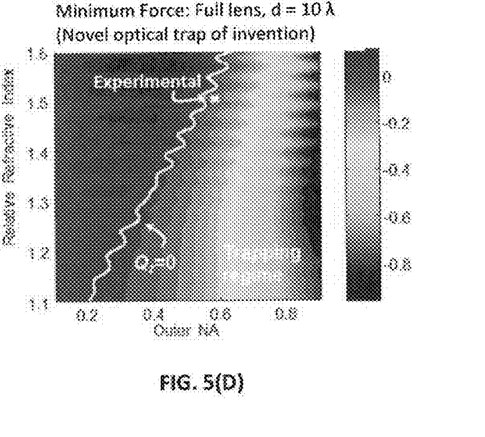

FIG. 5(C) shows the minimum trapping force obtained using the full lens and FIG. 5(D) shows the minimum trapping force obtained using the ring geometry with $NA_i=NA_o-0.05$. In both cases, the solid white contour line indicates $Q_z=0$ and trapping is possible to the right of the contour line. The oscillations as a function of refractive index are due to Mie resonances. Nonetheless, a comparison of FIGS. 5(C) and 5(D) shows that using the innovative ring geometry of the focused beam, optical trapping is possible using a much lower NA. (This is evident as the shift in the white contour line to the left corresponding to trapping with a lower NA). This advantage is particularly crucial when trapping relatively high index particles. The parameters of the particles trapped experimentally are indicated by a white "x" in FIGS. 5(C) and 5(D), showing that trapping particles with index of approximately 1.5 using a lens with NA=0.55 is only possible using the ring geometry.

Optical trapping is typically only possible if the force along the axial (z) direction becomes negative at some position, providing the restoring force required to hold a particle in place. Due to the relatively high index of the particle, the standard laser tweezers approach ("full lens") is not able to trap the particle, whereas the ring geometry provides a strong restoring force sufficient to trap the particle. The minimum trapping force, $min(Q_z)$, is shown using a full lens or the ring geometry as a function of the relative refractive index of the particle and the outer NA. For the ring geometry, the inner NA is set at $NA_i=NA_o-0.05$. The white contour lines correspond to $Q_z=0$ and optical trapping is possible when the minimum of $Q_z$ is negative (the "Trapping regime"). Using the ring geometry, optical trapping is possible using a much lower outer NA, enabling trapping of particles with an index of approximately 1.5 considered experimentally using an outer NA of only 0.55.

Figure 6A:
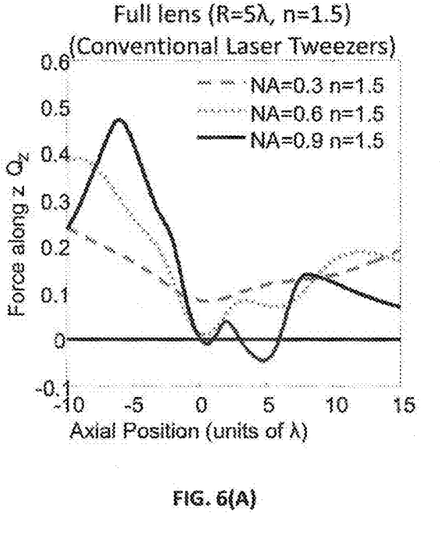
Figure 6B:
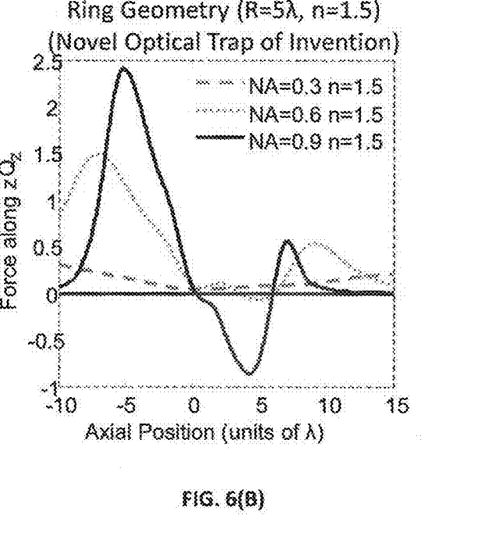
FIG. 6(B) shows the force for a ring illumination using the innovative optical trap of the present invention.

FIGS. 6(A) and (B) are plots showing the force along the optical axis experienced by a particle with radius of 5λ and n=1.5 for optical traps. FIG. 6(A) shows the force using a full lens, as in traditional laser tweezers, while FIG. 6(B) shows the force for a ring illumination, using the innovative optical trap of the present invention. In each case, the force using a lens with NA=0.3, 0.6, or 0.9 is shown. A negative force is required for trapping. Using standard laser tweezers, trapping is only possible using NA=0.9, but for the innovative optical trap, trapping is possible using NA=0.6 and NA=0.9. Based on the modeling, the NA for most embodiments, will most likely be at least 0.55 for N=1.5, typical for most glass material (it might be somewhat lower if the particle refractive index is smaller). It may be possible to trap particles using lower NA focusing optics, but that lowest limitation depends on the relative refractive index of the particles.

Based on the numerical simulations presented the plots in FIG. 5, the iris is adjusted to provide the optimal inner NA of approximately 0.5 based on the 0.55 outer NA of the aspheric lens. Optical trapping of four classes of airborne particles are experimentally demonstrated: absorbing and non-absorbing particles as well as spherical and spatially irregular particles. For this comparison, glass beads having a diameter of 3-9 µm were used as an example of a spherical, non-absorbing particle; 1-10 µm diameter albumin particles as an example of a non-absorbing spatially irregular particle; 6 µm diameter fluorescent polymer spheres as an example of a spherical absorbing particle; and 6.2-9.8 µm diameter Johnson smut grass spores as an example of a spatially irregular, absorbing particle. As further shown in FIG. 7, each particle type could be trapped and held stably in place for minutes to hours.

Figure 7:
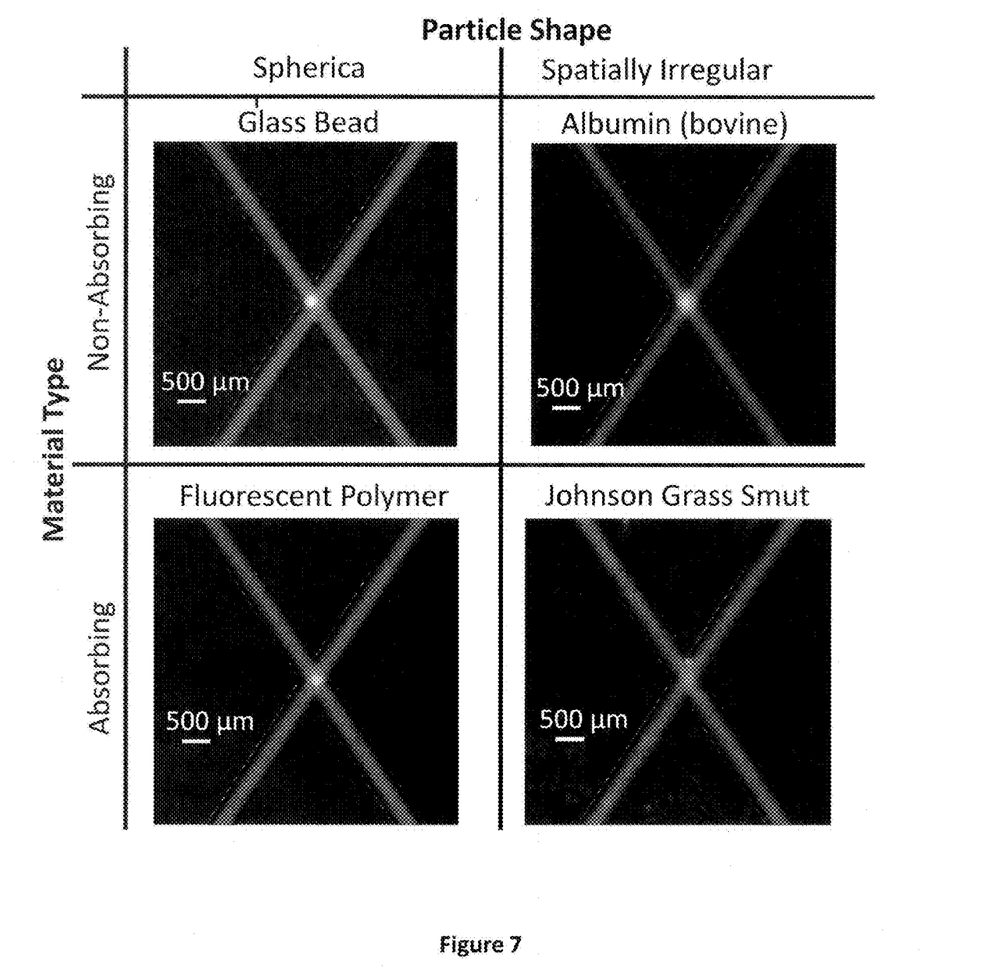
FIG. 7 shows optical trapping on four classes of particles, described by the particle shape (i.e. spherical or spatially irregular) and material type (i.e. absorbing or non-absorbing) using the optical trap according to an embodiment of the present invention.

FIG. 7 shows optical trapping on four classes of particles, described by the particle shape (i.e. spherical or spatially irregular) and material type (i.e. absorbing or non-absorbing). The images show an example of a trapped particle of each type. The transparent lines indicate the approximate position of the focal cone, as extracted from an image similar to the one shown in FIG. 4(A). Although the precise position of the focal spot changed slightly since the glass chamber was removed and cleaned after testing each particle type, all four particle types were trapped near the focal spot. The absorbing particles (the smut grass spores in particular), were also trapped in additional positions along the cone walls. It was found that each particle type could be trapped near the focal spot of the optical cone and held stably for minutes to hours. Moreover, the precise position of the trapped particles varied slightly depending on the size, shape, absorption of the particle, as well as the laser power. Nonetheless, particles of each type were trapped along the optical axis and could therefore by imaged to the entrance slit of a spectrometer in order to measure the fluorescence, Raman spectra, and other properties of a trapped particle.

Embodiments of the innovative optical trap may be used for various applications. For example, it may be used in a laboratory for in-vitro inspection and/or measurement of trapping particles. Or it may be incorporated into other airborne handing systems.

Figure 8:
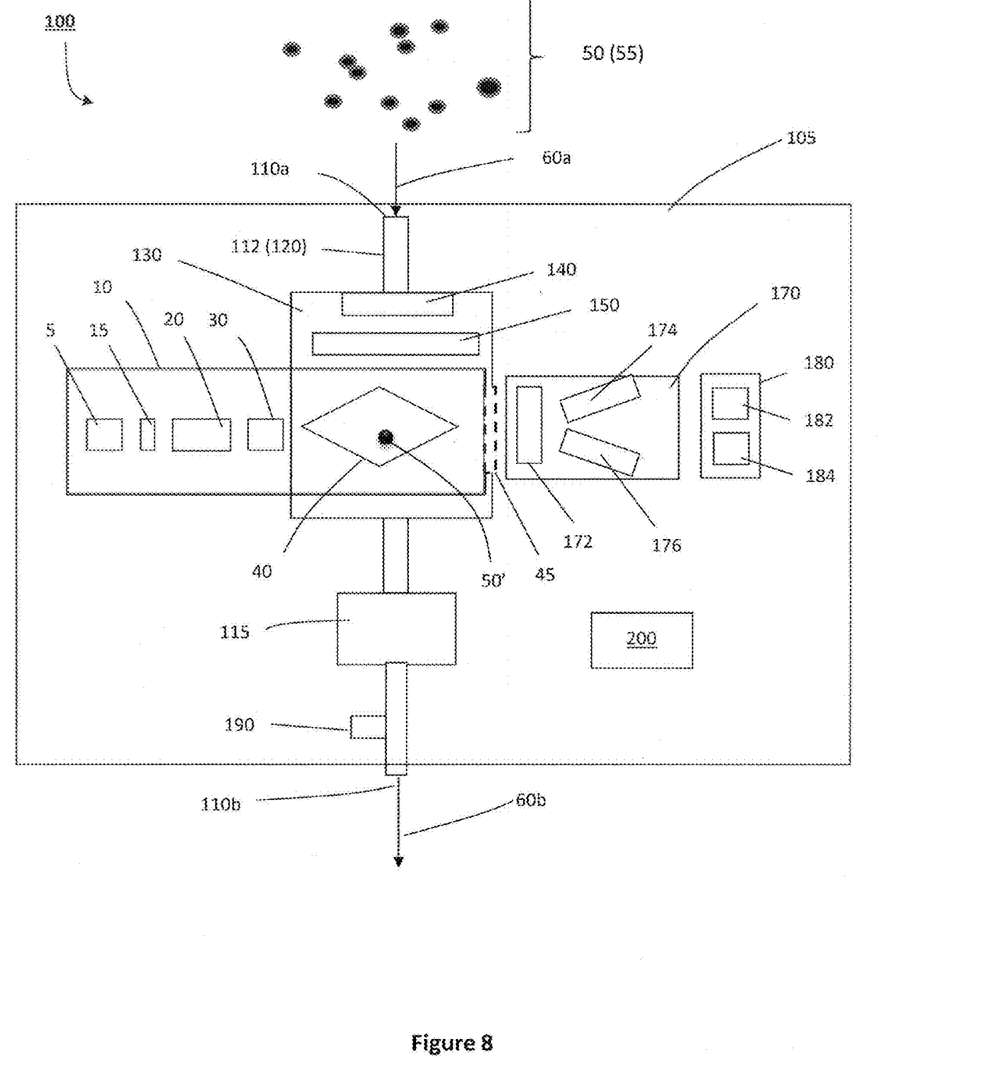
FIG. 8 shows a schematic illustration of an example system for continuously sampling airborne particles having an optical trap according to an embodiment of the present invention.

FIG. 8 shows a schematic illustration of an example system 100 for continuously sampling airborne particles according to an embodiment of the present invention. Various elements of the system 100 may be incorporated into a housing or other structure 105, thus forming a unitary apparatus. The housing 105 may also include an appropriate power supply, for instance. As such, the system, embodied as an apparatus, may provide a compact and portable device. In some embodiments, not all elements illustrated in the figure will be provided, and/or other elements may be provided. Additionally, it will be appreciated that the elements may be present or may be positioned in locations other than illustrated in this schematic.

Once inside the system 100, particles can be trapped and held using the optical particle trap 10 for inspection and/or measurements. The system 100 includes an airflow system 120 configured to draw one or more airborne particles 50 into a measurement volume 130. Inside the sampling volume 130 there is the trapping region 40. Particles within this trapping region 40 can be trapped and held for measuring, as explained later. The trapping region 40 may be defined by a glass containment cell.

The optical trap 10 is located within a sampling volume 130 of the system 100. For instance, in one embodiment, the sampling volume 130 and the trapping region 40 may be substantially the same size and overlap in a location within the system. In other embodiments, the trapping region 40 could be made relatively large and the sampling volume could be made small, and the air could be directed toward the optical trap 10. That arrangement may increase the fraction of particles, drawn into the device, that are caught in the trap, which can be beneficial for situations where the particles have been pre-selected in some way, or are expensive or hard to obtain.

Other measurements of properties (such as temperature, humidity, density, etc.) of the air drawn into the sampling volume 130, and/or of airborne particles 50 drawn into the sampling volume 130, and/or of the flow rate of the air drawn into the sampling volume 130 may be measured. Additional measurement(s) of particles 50, not requiring trapping individual particles 50', may also be measured in the sampling volume 130. Other configurations of the sampling volume 130 are also possible.

Particles 50 may be suspended in a gaseous medium 55 air, typically atmospheric air, or some other gas. In various implementations and uses, the particles may include, e.g., solid, liquid, gel, and/or mixtures of these dispersed in a gas, which may be consistent with the usual and customary definitions of aerosol particles. The system may be configured so that all the particles 50 drawn into the system pass through the trapping region 40, or it may be configured so that only a fraction of the particles are drawn through the trapping region 40. While a particle 40 is held in the trapping region 40 of the optical trap 10, airflow may continue substantially unabated through the trap 10, around the trap 10, or some combination thereof.

The airflow system 120 creates a flow of air 60. The incoming airflow 60a (to the system 100) flows into an inlet 110a and then to the sampling volume 130. The outgoing airflow 60b (from the system 100) flows via an outlet 110b to the ambient environment. A filter and/or grating (not shown) may be provided at the inlet 110a, if desired, to prevent particles larger than a predetermined size from entering the system. Passage 112 may provide fluid connection for airflow 60 through the system 100. A fluid mover 115 may be provided which creates sufficient force (e.g., negative pressure) to move the airflow 60 into and through the system 100. For example, the fluid mover 115 may be a pump, a fan, a compressor, a blower, a corona-generated ion wind, etc. To avoid violent or turbulent flow, the fluid mover 115 may be operated to ensure the flow rate of airflow 60 is laminar with a steady flow rate. To avoid large drag forces on particles, the airflow rates will typically be less than 1 m/s, and may be less than 1 cm/s. Lower airflow and particle velocities allow particles to be trapped with lower requirements for trapping laser power, for a given trap design. However, when the airflow rates are decreased, in order to reduce the requirements for trapping (such as, the trapping laser intensity), the sampling rate tends to decrease. While the fluid mover 115 is illustrated near the outlet 110b of the system 100, as it is a preferred embodiment because the particles do not need to pass through any fluid mover before they are measured. But, it will be appreciated that the fluid mover 115 can be located at another location in the airflow 50, such as, for example, near inlet 110a.

Inside the sampling volume 130, air and particles may pass through an optional particle concentrator 140 which increases the concentration or density of the particles in the airflow 60. The particle concentrator 140 may be a so-called "air-to-air" concentrator, for instance, for specifically processing particles in a gaseous medium.

A particle detector 150 is configured to detect a particle (or particles) approaching and/or within the sample volume 130. In one embodiment, the particle detector 150 may include one or more trigger beams. When a particle scatters light from the beam or beams, and this light is detected by one or more photodetectors, the signals from the photodetector or photodetectors indicate the presence of a particle either approaching and/or within the trapping region 40, depending upon the precise alignment of the trigger. As shown, the particle detector 150 is positioned somewhere upstream of the trapping region 40. But, in other embodiments, trigger beams of the particle detector 150 could overlap with the sampling volume 130 and/or the trapping region 40. For example, the particle detector 150 may be comprised of two different-wavelength crossed-beam diode lasers with corresponding photodetectors, each of said photodetectors including an optical filter that passes the wavelength of the diode laser it detects and blocks the light from the other diode laser and light at any other wavelengths that would interfere. One crossed diode trigger laser system which may be used as a particle detector 150 is described, for example, in U.S. Pat. No. 6,947,134, herein incorporated by reference. Of course, other trigger beam systems and devices might also be used for detection a particle. For detection of a particle within (not approaching) the trapping region, the particle detector 150 could at least partially overlap the trapping region 40 in the schematic drawing. Detector 150 also can be used to determine particle speed and size as an example.

The optical trap 10 generates light forces which trap an airborne particle and holds it. The light forces may be generated by the laser 5, are shaped by the iris 15, the optics 20, and the lens 30. The window 45 enables inspection and/or measurement into the trapping region 40. No mirror is shown here, but the optional mirror 25 could be positioned in the beam path as shown in FIG. 1 in some embodiments.

The optical trap 10 may operate as follows: 1) the trapping laser 5 is gated off (or turned "off", or modulated to a relatively low intensity, or blocked) for a short time (e.g., 1 ms) to let any trapped particle (typically as soon as the measurement of the trapped particle is completed) out of the trapping region 40, and to let new particles into the trapping region 40; 2) the trapping laser 5 is gated on (or turned "on", or modulated to be at a higher intensity) to trap any particle that is in the trapping region 40. After completion of the measurement(s), the process may be repeated, and in a typical embodiment is repeated continuously as soon as a particle is trapped and its desired properties have been measured. This approach may provide a less expensive, system by eliminating the separate trigger lasers and their associated photodetectors, filters, lenses and holders for this subsystem. The laser can also remain on at all times to trap one or a few representative particles for study and measurement, similar to the operating mode used in most conventional laser tweezer systems.

Optical forces generated by the optical trap 10 will tend to urge the particle 50' toward a focal point of the focused beam in the trapping region 40 of the optical trap 10; thus, the volume in which the particle is held during measurement of it optical properties is typically much smaller than the trapping region 40. Ideally, the trapping region 40 is sized and configured to trap and hold one individual particle 50' at a time from the airflow 60. It is noted that this is the expected performance of the optical trap 10.

However, there may be circumstances (e.g., relatively high concentrations of particles 50 in the inlet air) in which more than one particle might be trapped and held. This is a result of the typical substantially random distribution of particles in air. But the probability of trapping and holding two or more particles (e.g. greater than 0.5 micrometer) at once is likely to be very low (e.g., less than 1% of the time) if the average concentration of particles in air is low enough that only one particle is in the trapping region at any time. For instance, the particle concentration could be diluted by combining the inlet air with clean air, without any concentrator 140, at low inlet flow rate, or even by enclosing the inlet airflow within a clean air sheath. In any event, the optical trap 10 can be configured to trap and hold about one particle for measurement(s) thereof (i.e., where the vast majority of the measurements are of a single individual particle, and only some small fraction of the measurements are of two or more particles with sizes greater than some minimum diameter, e.g., 0.6 micrometer).

For some applications, embodiments that measure average spectra for multiple particles may be adequate, and in fact desired, for example, because the measurements could be made more quickly. For example, in monitoring the smoke particles from a fire, or the exhaust from an engine, trapping many particles at once, can provide a way to rapidly provide the average spectra of the particles, which may be desirable because, for example, such particles may change rapidly as the engine or fire parameters vary.

The trapping laser 5 is actuated (i.e., turned-on) or unblocked (or gated-on) or modulated to a higher intensity, for example, at an appropriate time to trap a particle. Various methods may be used to control the laser beam LB that generates the optical trap 10. If the trapping laser 5 is a diode laser that can be controlled by varying its drive current, then the beam amplitude (and trap) can be controlled by varying the drive current. And if the laser is one where the amplitude cannot be directly controlled sufficiently rapidly using fast electronics then other modulators or shutters could be used. For example, a separate blocking or modulating element (not shown) may be provided in various embodiments. This blocking or modulating element may be configured to be actuated so as to block the laser beam from reaching the trapping region 40. The blocking element could include, for instance, an acousto-optic modulator (AOM), electro-optic modulator (EOM), a motor-driven mechanical shutter, or a piezoelectric-driven shutter.

While a particle 50' is trapped and held in the optical trap 10, one or more properties of that trapped particle 50' may be measured or otherwise made. A measurement device 170 thus is configured to measure at least one property of the trapped particle 50' while it is held in the optical particle trap 10. These measurements may include, for example, Raman, fluorescence, thermal emission, laser-induced breakdown spectroscopy (LIBS), spark-induced breakdown spectroscopy (SIBS), image, particle morphology, elastic scattering over one, a few or many angles or wavelengths. The Raman, fluorescence, thermal emission, LIBS and SIBS may each be measured at one or more emission bands, including the case of sufficient bands to be considered a spectrum. The foregoing list is not exhaustive and other measurement techniques may be used. Devices for performing such measurements are generally known and will not be described in greater detail.

In one or more embodiments, Raman spectra (or Raman emission in one to several bands) of a trapped particle may be measured. Raman spectra provide information on the vibrational and rotational energy levels of molecules. These spectra can serve as "fingerprints" for various pure materials such as chemical warfare (CW) agent droplets, and may serve as fingerprints for some complex particles such as biological warfare (BW) aerosols prepared in certain ways, or certain species of fungal spores, etc. For these more complex particles such as those made from bacteria, the spectra tend to become more difficult to differentiate from spectra of similar bacteria grown under various conditions. More particularly, Raman spectral measurements may include, for example, Raman scattering, Raman spectroscopy, Resonance Raman spectroscopy, Coherent anti-stokes Raman scattering (CARS), and surface enhanced Raman scattering (SERS), which could be measured, for example, if the particles are combined with a droplet containing colloidal silver or gold nanoparticles before measurement).

Raman spectra may provide more information regarding the chemical and/or biochemical composition of individual airborne particles than can be obtained using ultraviolet laser-induced fluorescence (UV-LIF) even when the UV-LIF is combined with elastic scattering. According to one embodiment, the system may measure Raman spectra of particles at rates of 10's per minute to a few per second, depending upon the particle sizes, absorption coefficients, Raman cross sections, and concentrations of particles in air, etc. In general, Raman emission is generated when excitation electromagnetic energy (light) interacts with the molecules in a material. This excitation light generates a spectrum of light that has a different (e.g., typically longer) wavelength than the wavelength of the excitation light. The Raman emission spectra are usually characteristic of the material and generally exhibit peaks at wavelengths which depend upon the excitation wavelength and the frequencies of vibration and rotation of the molecules in the material.

At least one detector 172 may be included in the measurement device 170 for particle measurements. Typically in operation, only a fraction of the particles entering the system may be measured (although such operation is not limiting). The detector 172 can vary depending on which property of the trapped particle 50' is to be measured. General detectors and/or specific detectors may be used, for instance. In some embodiments, the detector 172 may include a spectrograph and the sensors.

Depending on the measurement desired, an excitation source may be required generate energy which can produce emissions and/or another phenomenon by the trapped particle 50'. In some embodiments, the same laser 5 that is used to trap the particle 50' may also be used to generate the excitation energy which causes the trapped particle 50' to generate the emissions and/or another phenomenon which is to be detected by the detector 172. For example, a portion of the beam of laser 5 may be split off from the rest of the beam (e.g., with a mirror, beamsplitter and/or other optics), manipulated and directed via optics to the trapped particle 50'.

In other embodiments, increased flexibility in trapping and measuring can be obtained by using one or more separate excitation sources 174. These sources, such as a laser, may be provided in the measuring device 170 that are configured to excite emissions of the trapped particle. As such, the trapping laser 5 need not be used in the measuring process. The excitation sources 174 may be operated at a different wavelength and/or other parameters than the trapping laser 5. For example, in some embodiments, the excitation sources may be focused tightly or weakly, depending on the application or mode of operation.

Collection optics 176 may further be included for manipulating emission and/or phenomenon to be measured by detector 172. These optics generally include some signal collection optics such as a lens, an objective, an elliptical mirror and a spherical mirror, and can use the same optics that form the trap. As an example of the elliptical mirror, the aerosol particle will be trapped at one of the focal points of the elliptical mirror, which has been positioned to coincide with the center of the spherical mirror. Therefore, light that reaches the spherical mirror from the particle is reflected back to the center of the mirror and towards the elliptical mirror, while light that reaches the elliptical mirror either directly from the particle or reflected from the spherical mirror is reflected to the second focal point of the elliptical mirror. This second focal point overlaps with the entrance of the spectrometer. This configuration enables collection of a large solid angle (e.g., greater than $2\pi$ or even $3\pi$ sr) of the Raman spectral emission from single particles, and it focuses the emission into a small angle to match the f-number of the Raman spectrometer.

A particle analyzer 180 is configured to analyze the measurement data. More particularly, the analyzer 180 may rapidly identify, determine, classify, characterize and/or sort, particles according to their measured properties. In some embodiments, it may determine, from at least one measured property, a parameter related to the trapped particle 50'. This may include determining from the measurements one or more parameters related to particle shape, size, refractive index, absorption, Raman cross section or any combination thereof of the trapped particle, for example. Parameters may be determined or otherwise computed from measured data. For instance, extracting the size, shape and refractive index of a particle from angular scattering measurements requires solving an inverse problem, or at least finding an approximation to that solution.

The particle analyzer 180 may be configured to monitor measurement data for potentially harmful particles such as bacteria, bacterial spores, pollens, fungal spores, protein allergens, smoke particles, and pollutants, such as pollutant particles that contain polycyclic aromatic hydrocarbons or reactive oxygenated species. A database (not shown) of known threats may be searched and/or analyzed with respect to measurement data, for example. Also, past measurements may be stored for further analysis and/or future searching.

In some instances, the particle analyzer 180 may be used to count and classify particles which can be used to determine or estimate exposures of persons to various airborne chemicals and pollutants, such as, for example, smoke from fires or burn-pits, or to diesel exhaust. The particle analyzer 180 may be a computer or microprocessor, for instance, which is configured to execute an algorithm 182 that is used to identify and or classify particles based on their measured properties, preferably in real time. The different categories can correspond to one or more different pollens, bacteria, bacterial spores, allergens or any other classification scheme. In some embodiments, the near-real-time algorithm used to classify particles into categories will be similar to those described in papers by R. G. Pinnick et al, "Fluorescence spectra of atmospheric aerosol at Adelphi, Md., USA: measurement and classification of single particles containing organic carbon," Atmos. Environ., 38, 657-1672 (2004); and by Y. L. Pan et al, "Single-particle laser-induced fluorescence spectra of biological and other organic-carbon aerosols in the atmosphere: measurements at New Haven, Conn., and Las Cruces, N. Mex.," J. Geophys. Res., 112, D24S19, 1-15 (2007), each of which is herein incorporated by reference. In other embodiments the near-real-time algorithm used to sort particles into categories may be the one described by Y. L. Pan et al, "Fluorescence spectra of atmospheric aerosol particles measured using one or two excitation wavelengths: Comparison of classification schemes employing different emission and scattering results," Optics Express, 18(12), 12436-12457 (2010), herein incorporated by reference. Of course, for the case of Raman spectra the algorithms may be the same or similar, but the actual spectral shapes for the different particle categories are very different, and generally will have higher information content. Again, for the case of thermal emission the algorithms may be the same as or similar to those described above, but the actual spectral shapes and spectral features that are used in the algorithms are different.

Additionally, the particle analyzer 180 may be coupled to a warning detector 184 that is configured to provide a warning when particles consistent with expected or known biological or chemical agents are detected. This may be instrumental, for instance, in the case of an attack with aerosolized biowarfare or chemical warfare agents by indicating a potential attack, so that personnel can begin to take protective actions. The warning detector 184 may include an audible alarm or siren, flashing (strobe) light, display screen, etc. which can provide audible and/or visual warnings. In some instances, written instructions may be provided by the display screen or printer for the aid of personnel. If the system is connected to a network (e.g., phone, internet, intranet, etc.) it may generate messages to contact first responders or other emergency personnel, command personnel and/or other persons, as desired.

A particle sorter 190 can physically sort, and optionally store, particles based on their measured properties. One particle sorting system which may be used with embodiments of the present invention is disclosed, for example, in U.S. Pat. No. 7,410,063, herein incorporated by reference. In other embodiments, once it is determined that a trapped particle should be collected and stored for further analysis, the air surrounding the particle is drawn though a filter (e.g., glass fiber, or filter with small holes (e.g., a nucleopore, or Millipore filter) by opening a valve connected to a vacuum or by turning on an air pump, and then catching the particle on the filter as the air it is entrained in is drawn through the filter.

A controller 200 is provided which is configured to the various control operations of the system 100, preferably in a fully-automated manner so that the system can trap a particle from air, hold it for as long as needed to measure its Raman spectrum or other properties as appropriate, then release the particle once the measurement(s) are completed, and then continuously repeat these steps (trap, measure, release). The controller 200 may be a computer or microprocessor, for instance, that includes computer-executable code which when executed is configured to implement methods for continuously sampling particles from air.

The controller 200 may be configured to generate and send signals to the various elements described herein, for instance, causing the elements to function or be otherwise actuated/deactivated upon command. This may include generating signals to: trap a particle in the sampling volume and hold the trapped particle; measure a property of the trapped particle; and release the trapped particle. The aforementioned sequence may be repeated as many times as desired.

Operation of the system 100 may vary depending on the particle detector 150, as discussed above. For example, in one embodiment, the controller 200 may generate a signal to actuate the optical trap 10 to trap the particle in the sampling volume 130 based on a detection signal received from the particle detector 150. Or, in another embodiment, the controller 200 may generate a signal to cause the measuring device 170 to measure a property of a trapped particle 50' already trapped in the optical trap 10 based on a detection signal received from the particle detector 150.

Once a particle is trapped by the optical trap 10, depending on the desired operation, controller 200 may ensure that it is held for sufficient time in order to: a) make one or more measurements of the same particle using different techniques; b) make improved measurements because the particle location can be better defined; and c) make measurements of dynamic processes in a trapped particle, by repeatedly measuring the spectrum or other parameter to see how it changes with time. In one embodiment, the fluorescence spectra can be measured with higher resolution, and the angular optical scattering can be measured with far better knowledge of the position of the particle and of the angles of the measured scattering intensities. The resulting reduction in uncertainties in the measurements makes the inverse problem, to extract parameters relating to the shape, size or chemical composition, far more tractable. Other sampling methodologies may also be executed, and the aforementioned ones should not be thought of as exhaustive.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, and to describe the actual partial implementation in the laboratory of the system which was assembled using a combination of existing equipment and equipment that could be readily obtained by the inventors, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

The invention claimed is:

1. An optical trap for trapping and holding both absorbing and non-absorbing airborne particles comprising:
   a trapping region where a particle can be present to be trapped;
   a light source for generating a coherent beam of light;
   optics for forming a hollow beam having a ring geometry from the coherent beam of light; and
   a focusing element for focusing the hollow beam to a point in the trapping region,
   wherein the particle is trapped at or near the focal point of the focused hollow beam.

2. The optical trap of claim 1, wherein the optics comprise: a pair of axicons, spatial light modulators (SLM), phase and amplitude mask, biaxial crystals, diffraction pattern, optical components configured to produce an aberration, and/or an interference pattern of coherent light source using a single or multiple laser beams to produce the hollow beam.

3. The optical trap of claim 1, further comprising an adjustable iris for controlling the inner diameter of the coherent beam of light.

4. The optical trap of claim 1, wherein the trapping region is located within a containment cell.

5. The optical trap of claim 1, further comprising a mirror positioned between the optics and the focusing element for changing the direction of the hollow beam.

6. The optical trap of claim 1, wherein the focusing element comprises an aspheric lens, an objective or a focusing mirror.

7. The optical trap of claim 1, wherein the focusing element has a numerical aperture (NA) less than or equal to 0.95.

8. The optical trap of claim 7, wherein the NA of the focusing element is 0.55-0.9.

9. The optical trap of claim 1, further comprising: a controller configured to control the trapping and holding of particles, wherein the controller is configured to generate signals to:
   trap one or more airborne particles in the trapping region;
   measure one or more properties of the one or more trapped airborne particles; and
   release the one or more trapped airborne particles.

10. The optical trap of claim 1, wherein the light source comprises a laser, a super-luminescent diode or a super-continuum source.

11. A particle detection and measuring system comprising:
   the optical trap of claim 1 for trapping and holding both absorbing and non-absorbing airborne particles;
   a particle detector configured to detect an airborne particle approaching and/or within the trapping region of the optical trap; and
   a measurement device to measure at least one property of the trapped particle.

12. The system of claim 11, wherein the optical trap is configured to trap and hold only about one particle at any one time.

13. The system of claim 11, further comprising: at least one source configured to excite emissions of the trapped one or more airborne particles.

14. The system of claim 11, wherein the measurement device is configured to measure one or more of: imaging, Raman spectra, Raman emission in one or more wavelength bands, laser-induced breakdown emission in one or more wavelength bands, laser-induced breakdown spectra, spark-induced breakdown emission in one or more wavelength bands, spark-induced breakdown spectra, fluorescence in one or more wavelength bands, fluorescence spectra, multi-photon excited fluorescence, thermal emission at one or more wavelengths, thermal emission spectra, or light scattering over one or more angles, light scattering at multiple wavelengths, absorption spectra of the particle, particle size and shape.

15. The system of claim 11, further comprising a particle analyzer configured to determine, from the measured property, a parameter related to particle shape, size, refractive index, absorption, or any combination thereof of the trapped one or more airborne particles.

16. The system of claim 15, wherein the particle analyzer is configured to execute an algorithm which identifies or classifies particles into different categories based on their measured properties.

17. The system of claim 16, further comprising: a particle sorter configured to physically sort, and optionally store, particles based on their measured properties.

18. A method for continuously sampling particles from air using the system of claim 11, the method comprising:
   continuously directing air including airborne particles toward a trapping region;
   detecting an airborne particle in the air approaching and/or within the trapping region;
   trapping one or more airborne particles in the optical trap;
   measuring a property of the trapped one or more airborne particles; and
   releasing the trapped one or more airborne particles.

19. The method of claim 18, further comprising: determining from the measured property a parameter related to particle shape, size, refractive index, absorption, molecular structures and compositions, chemical reactions, or any combination thereof of the trapped one or more airborne particles.

20. The optical trap of claim 1, wherein the hollow beam having a ring geometry includes an annular region with a central opening or void of no intensity.

21. The optical trap of claim 1, wherein the trap is formed of a single focusing beam of light.

* * * * *